US00PP35791P2

(12) United States Plant Patent
Valin

(10) Patent No.: US PP35,791 P2
(45) Date of Patent: May 7, 2024

(54) ***WEIGELA* PLANT NAMED 'TMWG19-108'**

(50) Latin Name: *Weigela florida*
Varietal Denomination: TMWG19-108

(71) Applicant: Branded Garden Products Ltd., Ipswich (GB)

(72) Inventor: Charles Valin, Ipswich (GB)

(73) Assignee: Branded Garden Products, Ltd, Ipswich (GB)

( * ) Notice: Subject to any disclaimer, the term of this patent is extended or adjusted under 35 U.S.C. 154(b) by 0 days.

(21) Appl. No.: 18/185,663

(22) Filed: Mar. 17, 2023

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new cultivar of *Weigela* plant named 'TMWG19-108' that is characterized by compact broad mounding plant habit, chartreuse colored yellow-green foliage, and deep red buds and flowers borne profusely in early spring, is disclosed.

1 Drawing Sheet

Genus and species: *Weigela florida.*
Variety denomination: 'TMWG19-108'.

BACKGROUND OF THE NEW PLANT

The present invention relates to a new and distinct cultivar of *Weigela*, grown as an ornamental plant for use in the garden and landscape. The new cultivar is known botanically as *Weigela florida* and will be referred to hereinafter by the cultivar name 'TMWG19-108'.

'TMWG19-108' originated from a *Weigela* breeding program which the inventor carried out at the inventor's nursery in Ipswich, United Kingdom. The inventor had assembled a collection of *Weigela* varieties (both commercial varieties and inventor's proprietary selections). After hand pollination between many of the assembled plants, seeds were collected, sown, grown on and planted in the field for evaluation. The identities of the parents of 'TMWG19-108' are unknown.

The new cultivar 'TMWG19-108' was selected in the field in 2018 by the inventor for its combination of bright yellow-green foliage with light grey-purple anthocyanin coloration to the younger leaves, and its red-purple flowers borne very profusely in spring. 'TMWG19-108' is a colorful accent plant in containers and in the landscape from spring through fall.

The inventor first asexually reproduced 'TMWG19-108' in 2018 by the method of softwood cuttings. The inventor has determined that the unique characteristics of 'TMWG19-108' are stable and reproduce true to type in successive generations of asexual reproduction.

SUMMARY

The following traits have been repeatedly observed and represent the characteristics of the new *Weigela* cultivar 'TMWG19-108'. 'TMWG19-108' has not been tested under all possible conditions and phenotypic differences may be observed with variations in environmental, climatic and cultural conditions, however, without any variance in genotype.

1. 'TMWG19-108' exhibits a compact broad mounding growth habit.
2. Mature fully flowering plants of 'TMWG19-108' achieve a height of 50 cm. to 55 cm. and a width of 75 cm. to 80 cm.
3. The spring foliage of 'TMWG19-108' is predominantly yellow-green in color tinged with light grey-purple anthocyanin coloration especially on the underside of the younger leaves.
4. Plants of 'TMWG19-108' are extremely floriferous in early to mid-spring.
5. A mature plant of 'TMWG19-108' bears approximately 50 flowering stems, each with three whorls of 6 flowers (occasionally 4 flowers) in each whorl.
6. A mature plant of 'TMWG19-108' bears approximately 900 buds and flowers at peak flowering in spring.
7. The flowers and flower buds of 'TMWG19-108' are red-purple in color.
8. 'TMWG19-108' grows well in moist well-drained soils in full sun to partial shade.
9. 'TMWG19-108' is hardy at least to USDA Zone 5.

BRIEF DESCRIPTION OF THE PHOTOGRAPH

The accompanying color photograph illustrates the overall appearance of the new *Weigela* variety 'TMWG19-108' showing colors as true as it is reasonably possible to obtain in colored reproductions of this type. Colors in the photographs may differ from the color values cited in the detailed botanical description, which accurately describe the actual observed colors of 'TMWG19-108'.

The photograph depicts a whole plant of 'TMWG19-108' in mid-April in full flower in Santa Barbara, California. The illustrated plant is three years old and is growing in a 3.7-gallon container. The illustrated plant has been grown entirely outdoors in Santa Barbara, California. No chemicals were used to treat the plant.

BOTANICAL DESCRIPTION OF THE PLANT

The following is a detailed description of the new cultivar 'TMWG19-108'. Data was collected in mid-April from fully flowering three-year old plants grown in 3.7-gallon (14 liter) containers in Santa Barbara, California. The color determinations are in accordance with the 2007 edition of The Colour Chart of The Royal Horticultural Society, London, England, except where general color terms of ordinary dictionary significance are used. No chemicals were used to treat the plants. Growing conditions are typical of other *Weigela*.

Botanical classification: *Weigela*.

*Variety*.—'TMWG19-108'.

*Species*.—*Florida*.

Parentage:

*Female parent*.—Unknown.

*Male parent*.—Unknown.

Plant description:

*Growth habit*.—Compact, broad mound.

*Use*.—In containers and in the landscape.

*Suitable container sizes*.—1 gallon, 3 gallon and larger.

*Dimensions*.—50 cm. to 55 cm. in height, and 75 cm. to 80 cm. in width.

*Hardiness*.—At least hardy to USDA Zone 5.

*Propagation*.—Stem cuttings.

*Time to initiate roots*.—5 to 6 weeks are required to produce roots on an initial cutting.

*Crop time*.—9-10 months to produce a first year flowering plant in a small container. Additional years to produce larger specimen plants.

*Root system*.—Fibrous.

*Light*.—Plant in full sun or partial shade.

*Soil*.—Plant in moist but well drained soil.

*Type*.—Deciduous shrub.

*Seasonal interest*.—Extremely floriferous in early-mid spring.

Stem (below first pinch or stop):

*Shape*.—Terete.

*Dimensions*.—10 cm. to 12 cm. in length, 1.0 cm. to 1.5 cm. in diameter at soil level.

*Color*.—N200B

*Surface*.—Lignified, rough, lenticels present.

*Lenticels*.—spaced approximately 2 mm. to 8 mm. apart, elliptic, length 1.5 mm., width 1.0 mm., slightly raised (less than 0.5 mm.), color 202B.

Branches:

*Quantity*.—Approximately 50 primary and lateral branches.

*Branch stem dimensions*.—45 cm. to 50 cm. in length, 5 mm. to 8 mm. in diameter.

*Shape*.—Terete.

*Internode length*.—3 cm. to 5 cm.

*Color*.—161B.

*Surface*.—Smooth, lenticels where present (lower internodes only) spaced approximately 2 mm. to 8 mm. apart, elliptic, length 1.5 mm., width 1.0 mm., slightly raised (less than 0.5 mm.), color 202B.

Foliage:

*Leaf arrangement*.—Opposite.

*Leaf division*.—Simple.

*Leaf shape*.—Ovate, longitudinally inwardly curved.

*Leaf attachment*.—Short petiolate.

*Petiole shape*.—Sulcate, adaxial surface concave.

*Petiole dimensions*.—2 mm. to 3 mm. in length and 2.5 mm. in width.

*Petiole color*.—154D, margins 67A.

*Leaf dimensions*.—55 mm. in length, 26 mm. in width.

*Leaf surface* (*adaxial*).—Glabrous.

*Leaf surface* (*abaxial*).—Glabrous, except pubescent and towards base, hairs fine, less than 0.5 mm in length, hair color 156C.

*Leaf color* (*newly emerged leaves, early spring, both surfaces*).—154B.

*Leaf color* (*solar-facing surfaces, newly emerged apical leaflets*).—Orange-brown anthocyanin tinges 187D and lighter than 187D.

*Leaf color* (*both surfaces, late spring, summer and into fall*).—144B.

*Leaf color* (, *both surfaces, fall*).—153B.

*Leaf apex*.—Acuminate, tip color N186D.

*Leaf base*.—Cuneate.

*Leaf margin*.—Finely serrate, glabrous except leaf margin pubescent towards base, hair color 156C, hair length 1.0 mm. to 1.5 mm. Margin color 64A.

*Leaf venation pattern*.—Pinnate.

*Veins* (*adaxial surface*).—Prominent midrib, slightly raised, color 154D.

*Veins* (*abaxial surface*).—Prominent midrib, increasingly raised towards base, color 160B, tinged 64A.

Inflorescence, flowers:

*Inflorescence form*.—Cymose.

*Flowers arrangement*.—Flowers present at each leaf axil in whorls of six flowers or, very occasionally, four flowers per whorl.

*Quantity of flowers per plant*.—Approximately 900 flowers at peak flowering (6 flowers per whorl, 3 whorls per stem, 50 stems per plant).

*Flower aspect*.—Initially (buds and first opening) outward and upward facing, becoming horizontal and downward facing as flowers mature and age.

*Diameter of fully developed flower* (*at flower tube apex*).—28 mm. as presented, 35 mm. measured when flattened.

*Length of flower, including corolla tube*.—35 mm. to 40 mm.

*Bud*.—Shape: Cylindrical, apex capitate. Color: 187A. Dimensions: 25 mm. in length, 7 mm. to 10 mm. in diameter immediately prior to opening. Surface: Faintly puberulent.

*Bracteoles*.—Arrangement: Borne in unequal pairs the base of peduncle. Shape: Narrowly lanceolate. Dimensions: Longer bracteole 6 mm. in length, shorter bracteole 3 mm. to 4 mm. in length, both bracteoles 1 mm. in width at base. Color: 160B, tinged 64A. Surface: Glabrous.

*Peduncle*.—Dimensions (buds): 12 mm. in length and 1 mm. in diameter. Dimensions (flowers): 16 mm. in length and 1 mm. in diameter. Shape: Round. Color: 59A (buds), 53A (flowers). Surface: Smooth, glossy.

*Calyx, sepals*.—Shape: Narrow funnel-shaped. Calyx diameter: 6 mm. measured across sepal apices. Sepals: 5 in number, fused towards and at base. Sepal dimensions: 8 mm. to 11 mm. in length, 2 mm. in width. Sepal color (both surfaces): 185B. Sepal surface (both surfaces): Matte, puberulent.

*Corolla* (*tube and fused petals to base of free petal lobes*).—Shape: Salverform. Dimensions: 28 mm. in length, 2 mm. in diameter at base, 13 mm. in diameter at base of petal lobes. Surface: Glabrous. Tube color: Adaxial surface: 60A. Abaxial surface: 60C to 60D.

*Petals* (*free petal lobes*).—Number: 5, fused at base. Petal lobe shape: Orbicular. Petal margins: Undulating and lightly crenate with occasional semicircular marginal notches approximately 0.5 mm in depth and width. Margins smooth. Color (adaxial surface): 60A. Color (abaxial surface): 60C to 60D. Surface texture: Glabrous.

Reproductive organs:

*Number of stamens.*—5, individually fused to corolla tube at base.

*Dimensions (filaments).*—13 mm. in length, 5 mm. where fused, 8 mm. free; diameter 0.75 mm. to 1.0 mm. in diameter.

*Filament color.*—70C where fused, becoming N155A where free.

*Anther shape.*—Narrow elliptical, apex bifid.

*Anther dimensions.*—5 mm. in length and 0.75 mm.-1.0 mm. in width.

*Anther color.*—161C to 161D.

*Pollen amount.*—Predominantly none. Moderate amount on a few flowers.

*Pollen color.*—158C.

*Number of pistils.*—1.

*Style.*—Round, 35 mm. in length and 1 mm. in diameter.

*Style color.*—70C towards base, becoming N155A towards stigma.

*Style surface.*—Glabrous.

*Stigma shape.*—Capitate.

*Stigma dimensions.*—4 mm. in diameter and 2 mm. in height.

*Stigma color.*—155A with faint ring 70C around abaxial attachment to style.

*Ovary.*—Observed immature only (absent on most flowers): Superior, ovoid, 1.5 mm. in length and 1 mm. in diameter, color 59A, smooth, glossy.

Fruit: None observed.

Seed: None observed.

Susceptibility or resistance to pests and diseases: None.

COMPARISON WITH PARENT VARIETIES

The parents of 'TMWG19-108' are unknown. No comparison is available.

COMPARISON WITH KNOWN VARIETY

'TMWG19-108' may be compared with the widely grown *Weigela* variety 'Rubidor' (unpatented). Both 'TMWG19-108' and 'Rubidor' bear chartreuse colored yellow-green foliage and dark red flowers. However, the leaves of 'TMWG19-108' are darker overall and the newly emerged leaves of 'TMWG19-108' are bronzed on their undersides. In addition, whereas 'TMWG19-108' is a compact and low growing variety, 'Rubidor' grows to at least 1.5 m. to 2 m. in height.

I claim:

1. A new and distinct cultivar of *Weigela* Plant Named 'TMWG19-108' as described and illustrated herein.

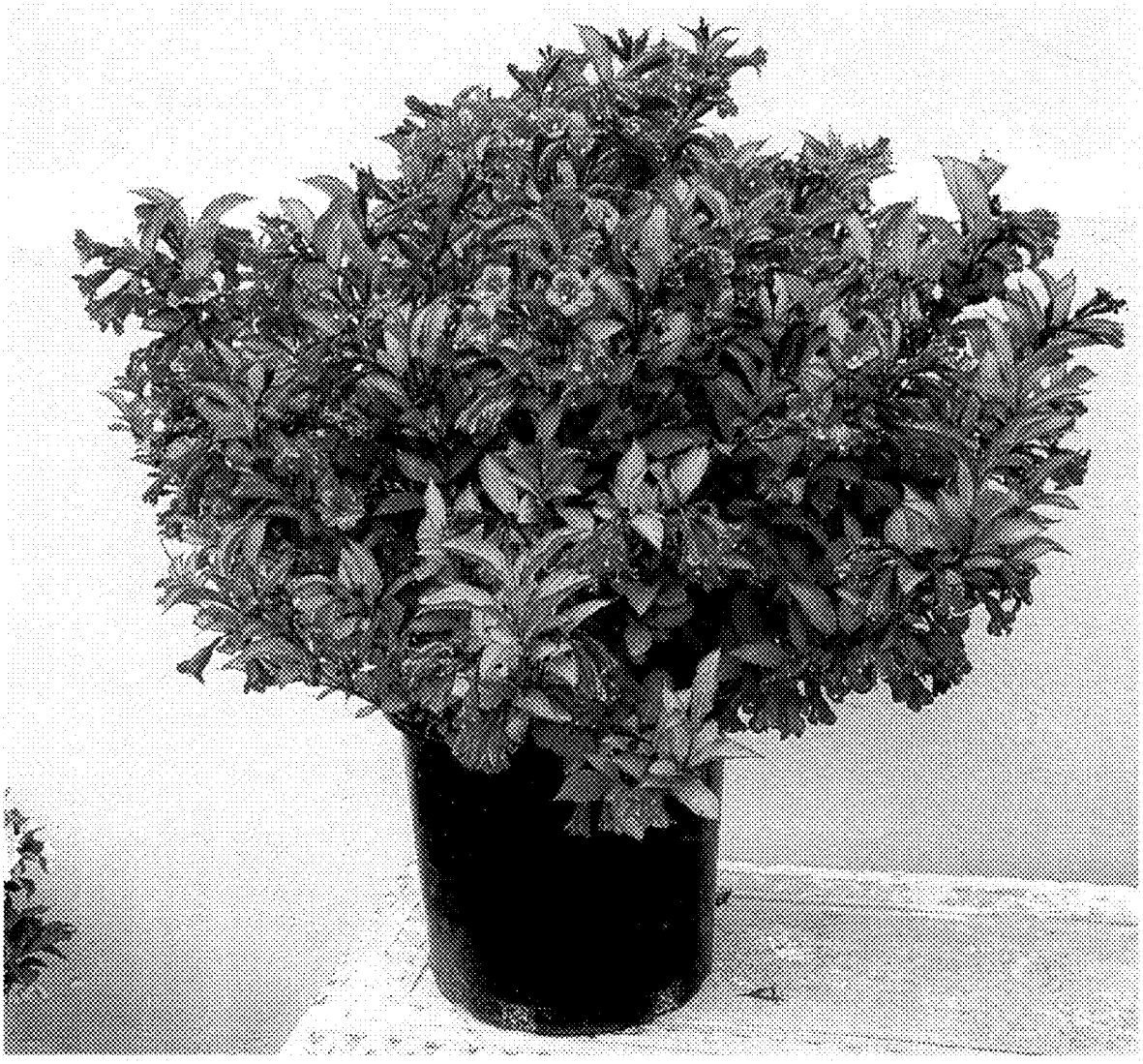

* * * * *